United States Patent [19]

O'Brien et al.

[11] Patent Number: 4,679,221
[45] Date of Patent: Jul. 7, 1987

[54] CT X-RAY COLLIMATOR INCLUDING A REINFORCED COLLIMATOR BLADE ASSEMBLY

[75] Inventors: Thomas P. O'Brien, Deerfield; Richard T. Bernardi, Prospect Heights, both of Ill.

[73] Assignee: Kabushiki Kaisha Toshiba, Kawasaki, Japan

[21] Appl. No.: 763,624

[22] Filed: Aug. 8, 1985

[51] Int. Cl.⁴ .......................... G21K 1/02; G21K 3/00
[52] U.S. Cl. ..................... 378/148; 378/157; 378/146
[58] Field of Search ................ 378/15, 10, 4, 147, 378/148, 157, 158, 146, 153

[56] References Cited

U.S. PATENT DOCUMENTS

| | | | |
|---|---|---|---|
| 1,704,974 | 3/1929 | Katzman | 378/147 |
| 2,468,963 | 5/1949 | Dudley | 378/146 |
| 2,670,401 | 2/1954 | Weinberg | 378/146 |
| 4,277,685 | 7/1981 | Covic et al. | 378/157 |
| 4,506,374 | 3/1985 | Flynn | 378/149 |

*Primary Examiner*—Craig E. Church
*Assistant Examiner*—T. N. Grigsby
*Attorney, Agent, or Firm*—Finnegan, Henderson, Farabow, Garrett & Dunner

[57] ABSTRACT

A collimator blade assembly for a computed tomographic X-ray scanner comprising a blade of X-ray beam stopping material having an aperture for passing X-rays and an X-ray penetrable member closing at least a portion of that aperture to reinforce the material and thereby minimize collimator blade/detector clearances while preventing undesirable collimator blade vibration.

12 Claims, 7 Drawing Figures

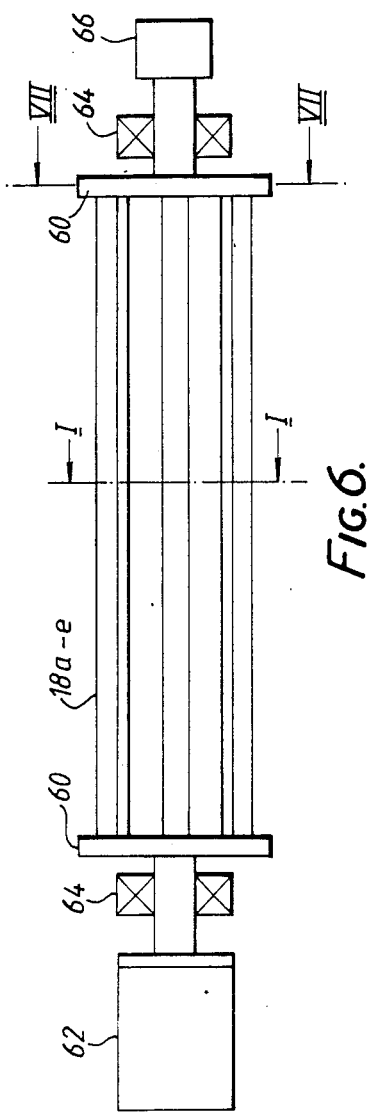
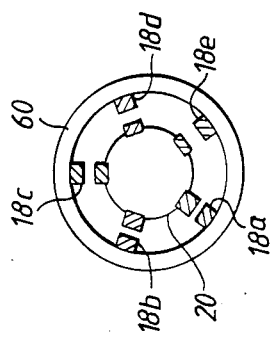
FIG. 6.
FIG. 7.

CT X-RAY COLLIMATOR INCLUDING A REINFORCED COLLIMATOR BLADE ASSEMBLY

BACKGROUND OF THE INVENTION

I. Field of the Invention

The present invention relates to collimators and components thereof for use in computed tomographic (CT) X-ray scanners and components thereof.

II. Background Information

A variety of fourth generation CT scanners require rotation of an X-ray source with simultaneous nutation of a detector ring. The nutation motion of the detector ring permits a clear path from the X-ray source to the oppositely positioned interior surface of the detector ring through movement of the near portion of the detector ring away from that path. A pre-patient collimator may be employed in conjunction with the X-ray source which comprises a slab or blade of beam stopping material having a longitudinal slot for passing X-rays from the source to the target area of the patient. However, the nutating motion of the detector ring results in a minimum amount of clearance between the collimator blade and detector ring in order to minimize the nutation angle at which the detector ring is tilted.

A pre-patient collimator constructed of a blade of X-ray beam stopping material having a longitudinal slot therein has been constructed by the inventors with the proximity of the slot to the lengthwise edge of the blade minimized in order to minimize the clearance between the collimator blade and the detector ring. However, the resultant narrow section of the collimator blade between the slot and detector ring has been found to vibrate. This vibration has been found to occur at fundamental frequencies which are typically on the order of 100 hertz. This means that the narrow section of the collimator blade might easily be driven into unacceptable vibration by normal gantry vibrations, thereby producing beam intensity modulation which will degrade image quality unless complex corrections are made.

It is, accordingly, an object of the present invention to provide a collimator which has a blade with a section narrow enough to minimize the nutation angle of a detector ring of a fourth generation CT scanner and yet avoid unacceptable vibration due to typical gantry vibrations.

Additional objects and advantages of the invention will be set forth in the description which follows and in part will be obvious from the description or may be learned by practice of the invention.

SUMMARY OF THE INVENTION

To achieve the foregoing objects, and in accordance with the purposes of the invention as embodied and broadly described herein, a collimator for a CT X-ray scanner is provided which comprises a collimator blade assembly including a blade comprised of an X-ray beam stopping member having an aperture for passing X-rays and having an X-ray penetrable member closing at least a portion of that aperture to reinforce the beam stopping material.

In different words, an embodiment of the collimator blade assembly of the subject invention maybe said to comprise a generally rectangular slab or blade of X-ray beam stopping material having a longitudinal slot therebetween for passing X-rays from a source to a target and means for minimizing vibration of the blade while maximizing the proximity of the slot to a lengthwise edge of the blade, this means comprising an X-ray penetrable reinforcing member fixed to the blade to extend transversely across at least a portion of the slot.

Preferably the X-ray penetrable member comprises X-ray penetrable materials selected from the group consisting of plastic, beryllium, graphite reinforced epoxy, and aluminum. In the alternative, the X-ray penetrable member, in addition to passing X-rays in a selected energy region of the X-ray spectrum, also absorbs X-rays in a selective energy region of the X-ray spectrum. In this embodiment of the subject invention the X-ray penetrable member preferably comprises X-ray penetrable materials selected from the group consisting of copper, stainless steel and titanium.

It is also preferable that the collimator include a plurality of the above-mentioned collimator blade assemblies mounted in a rotatable star configuration.

BRIEF DESCRIPTION OF THE DRAWINGS

FIG. 6 is a side view of the pre-patient collimator illustrated in FIG. 1 and

FIG. 7 is an end view of the collimator of FIG. 6 taken along Section VII—VII.

DESCRIPTION OF THE PREFERRED EMBODIMENT

Figure 1:
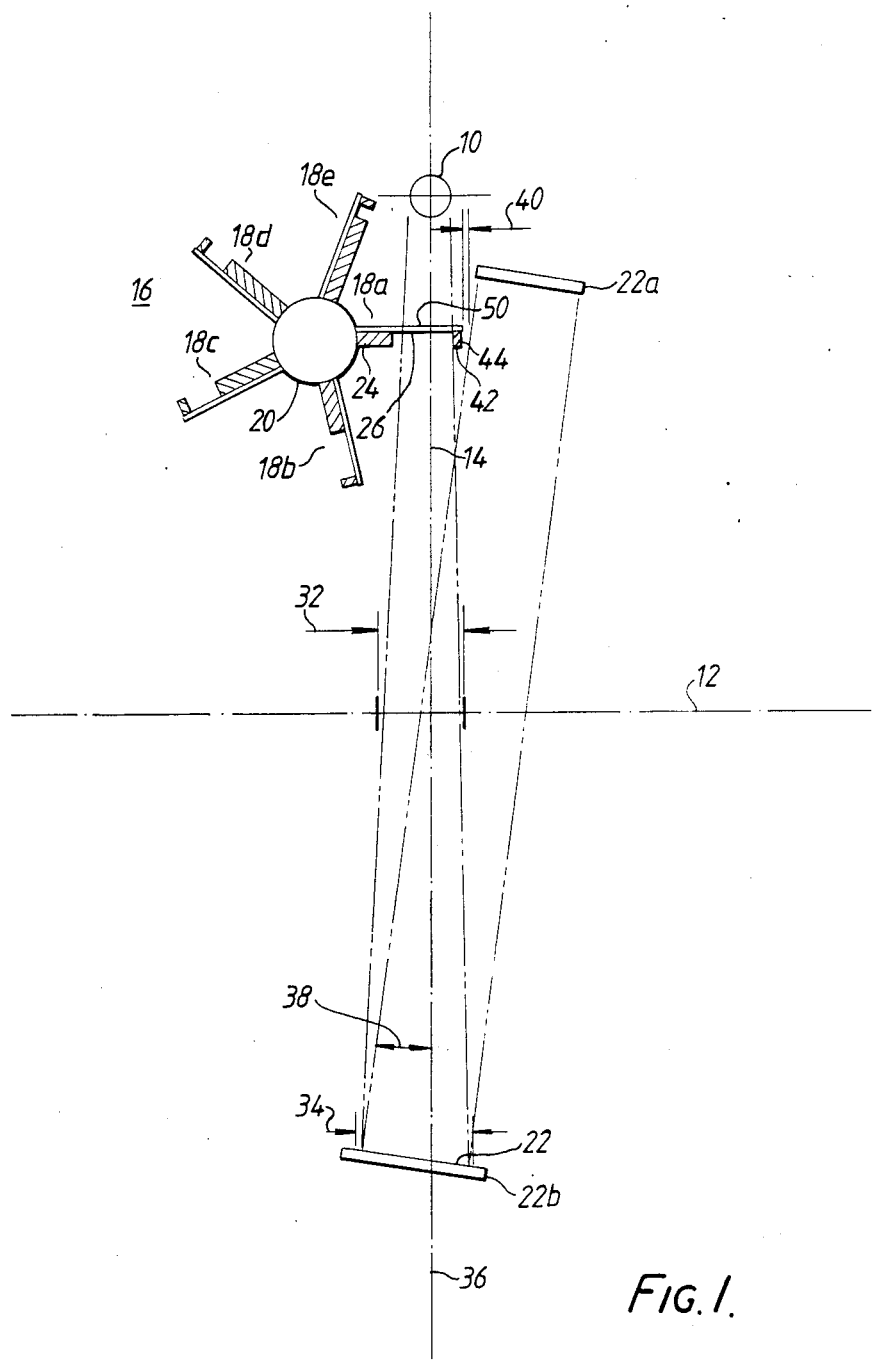
FIG. 1 is a cross-sectional view of a CT X-ray scanner showing the relationship between a pre-patient collimator incorporating the teachings of the subject invention and a nutating detector ring.

In FIG. 1 there is shown an X-ray source 10 of a fourth generation CT scanner of the rotate/nutate type. As should be appreciated by those skilled in the art, X-ray source 10 rotates about a gantry center line of rotation 12 in a plane perpendicular to the plane of FIG. 1. In the position illustrated in FIG. 1, X-ray source 10 emits X-rays in the form of a narrow width, elongated length fan beam 14. Beam 14 is shaped by a collimator 16 which includes a plurality of collimator blade assemblies 18a–e which are mounted in a star-shaped configuration to a rotatable axle 20. Each collimator blade assembly 18a–e shapes beam 14 to strike an oppositely facing inside surface of detector ring 22.

Collimator blade assemblies 18a–e each include a collimator blade 24 which is preferably constructed of a general rectangular slab or blade of beam stopping high Z collimator material such as machinable tungsten which, as is known to those skilled in the art, is impervious to substantially all, if not all, X-ray output from source 10. Each collimator blade 24 has an aperture 26 shaped in the form of a longitudinal slot. Accordingly, the only X-rays from source 10 capable of reaching detector ring 22 are those which pass through an aperture 26 of an X-ray impenetrable blade 24 of a particular collimator beam assembly 18a–e aligned with beam 14 of source 10.

Each collimator blade 24 may be constructed of a single piece of material in which aperture 26 is formed, or each collimator blade 24 may be constructed of several pieces of material which are joined at their ends to form aperture 26.

Figure 2:
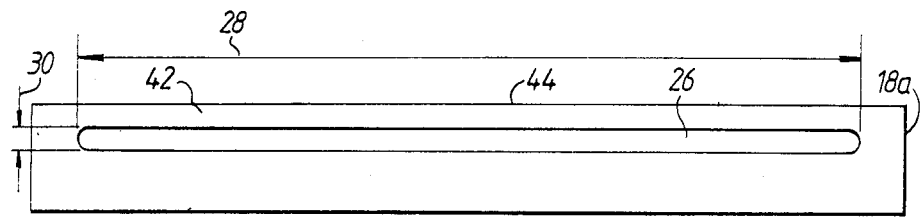
FIG. 2 is a top view of a portion of the collimator blade assembly illustrated in FIG. 1.

A top view of one collimator blade assembly 18a is illustrated in FIG. 2. As is illustratively shown in FIG. 2, the length 28 of aperature 26 may be substantially greater than the width 30 of aperture 26. As a result, aperture 26 when aligned with source 10 forms a thin X-ray fan beam 14 with a predetermined diagnostic slice width 32 along center line of rotation 12 as shown in FIG. 1. The magnitude of slice width 32 may be varied by selecting a different width 30 of aperture 26 for each collimator blade assembly 18a–e. Given the geometries of the width 30 of aperture 26 for any collimator blade assembly 18a–e, fan beam 14 has a corresponding width 34 at the surface of detector ring 22. The length of fan beam 14 at the surface of detector ring 22 is governed by the length of aperture 26. The exposed edges of blades 24 which form aperture 26 should have a smooth ground blade edge finish to eliminate any circular CT image artifacts that could result from scratches on the exposed edges of the collimator blade. Widths 30 for blade assemblies 18a–e may be 10, 5, 3, 2, and 1 mm, respectively.

As shown in FIG. 1, detector ring 22 is of the nutating type. That is to say, detector ring 22 is not aligned along scan center line 36, but rather is aligned at nutation angle 38 to permit that portion 22a of detector ring 22 which is closest to source 10 to avoid the path of fan beam 14 and thereby permit fan beam 14 to strike the inside surface of that portion 22b of detector ring 22 furthest away from source 10. While nutate angle 38 permits source 10 to be located outside of the circumference of detector ring 22 and thereby permits utilization of a relatively small detector ring, the tilting of detector ring 22 from scan center line 36 as a result of nutate angle 38 causes fan beam 14 to strike detector ring 22 at an oblique angle thereby causing distortion. Moreover, as nutate angle 38 increases, the mechanisms required to effect nutation increase in size and expense. For these reasons, it is preferable to minimize the size of nutate angle 38. However, the size of nutate angle 38 dictates the clearance 40 between any source-aligned collimator blade 24 of assemblies 18a–e and detector ring 22. To minimize nutate angle 38, clearance 40 must be minimized.

To accomplish minimization of clearance 40, the slab of X-ray beam stopping material which comprises collimator blade 24 may be designed to include a narrow section 42. Use of a narrow section 42 maximizes the proximity of aperture or slot 26 to the lengthwise edge 44 of collimator blade 24, thereby minimizing clearance 40. However, narrow section 42 may very well have a fundamental frequency of vibration which is quite low, for example, below 100 hertz. This means that narrow section 42 of collimator blade 24 could be driven into unacceptable vibration by normal gantry vibrations set up through normal gantry operation. This collimator blade vibration may produce beam intensity modulation at surface 22b of detector ring 22 which will degrade the resultant image quality unless complex corrections were made.

In order to solve this troublesome problem and in accordance with the teachings of the present invention, each collimator blade assembly includes means for minimizing vibration of each collimator blade, while maximizing the proximity of a longitudinal slot within that blade to a lengthwise edge of the blade, which comprises an X-ray penetrable reinforcing member affixed to the blade to extend transversely across at least a portion of the slot.

Figure 3:
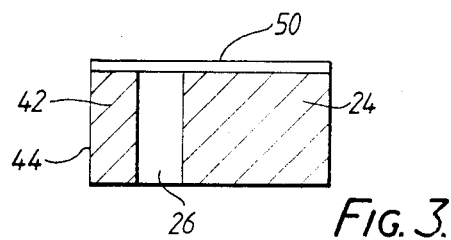
FIG. 3 is a side view of one embodiment of the portion of a collimator blade assembly illustrated in FIG. 2 taken along section AA.

For example, as shown in FIGS. 1 and 3, a reinforcing member 50 is affixed to one exposed surface of the slab of X-ray beam stopping material which comprises collimator blade 24 in a manner whereby member 50 extends transversely across at least a portion of slot or aperture 26. Reinforcing member 50 is preferably a flat plate laminated or bonded to an exposed surface of collimator blade 24 through adhesive bonding, brazing, welding or the like. Reinforcing member 50 preferably consists of a material having very low X-ray absorption such as plastic, beryllium, graphite reinforced epoxy or aluminum. However, other materials could also be used to form reinforcing member 50 which, although X-ray penetrable in a portion of the X-ray spectrum, are X-ray absorptive in another portion of the spectrum, expecially in the low energy region of the X-ray spectrum. Such materials may, for example, include copper, stainless steel or titanium. The use of an at least partially X-ray absorptive material has the advantage of producing spectral changes in the X-ray output, that is, of filtering the X-ray output. Thus, a dual function may be achieved by reinforcing member 50, that of reinforcing the narrow section 42 of blades 24 and also a filtering function.

As should be appreciated, reinforcing member 50 preferably extends along the entire length 28 of aperture 26 to provide maximum support for narrow section 42 and thereby reinforce the slab of high Z collimator material which comprises collimator blades 24. However, one or more sections of aperture 26 might be transversed by reinforcing member 50 without having the entire aperture 26 closed off by reinforcing member 50.

Figure 4:
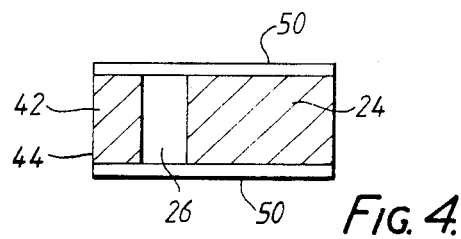
FIG. 4 is a side view of another embodiment of the portion of a collimator blade assembly illustrated in FIG. 2 taken along section AA.
Figure 5:
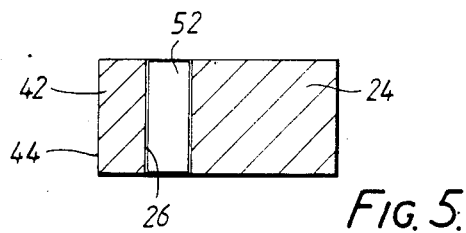
FIG. 5 is still another embodiment of the portion of a collimator blade assembly illustrated in FIG. 2 taken along section AA.

In FIG. 4, two reinforcing members 50 are shown affixed on opposite facing exterior surfaces of collimator blade 24. In another alternative embodiment shown in FIG. 5, a reinforcing member 52 comprised of the same material as reinforcing members 50 in the previous embodiments, might be bound or otherwise affixed to the interior surfaces of collimator blade 24 which define aperture 26 and thereby extend across or close at least a portion, if not all, of aperture 26 while reinforcing the overall structure of collimator blade 24.

Although flat exterior surfaces of collimator blades 24 have been illustrated, it is contemplated that curved surfaces might also be encountered and reinforcing members affixed to those curved surfaces to thereby extend across at least a portion of a collimator aperture to thereby reinforce the overall collimator blade structure.

As noted above, a plurality of collimator blade assemblies may be mounted on a rotatable axle 20 in a star-shaped configuration. For example, as is shown in FIGS. 2, 6 and 7, five collimator blade assemblies 18a–e are mounted lengthwise along an axle 20 to project outwards at intervals of 72 degrees. As shown in FIGS. 6 and 7, the ends of each blade assembly 18a–e are supported by a circular disc support member 60. The outer edge of each member 60 may extend beyond the outer edges of blade assemblies 18a–e since the ends of blade assemblies 18a–e extend beyond detector ring 22. Thus, nutate angle 38 (as shown in FIG. 2) is not affected by the size of members 60.

A motor 62, bearings 64 and encoder 66 may be used to respectively rotate, support and locate collimator blade assemblies 18a–e. The required angular repeatability needed to maintain constant slice widths can be achieved with the use of either an open-looped stepped-motor control with accuracy of one step at 0.09 degrees per step, or a closed-loop control with the use of an incremental encoder 66 with the same or greater degree of repeatability. A collimator using one or more collimator blade assemblies of the subject invention thereby permits maximizing the proximity of a slot or other form of aperture to one lengthwise edge of the blade containing that aperture while minimizing mechanical vibration of that blade. Thus, collimator blade/detector ring clearance can be minimized without unacceptable collimator blade vibration, thereby permitting utilization of a minimal nutation angle in a fourth generation CT scanner of the rotate/nutate type.

Additional advantages and modification will readily occur to those skilled in the art. The invention in its broader aspect is, therefore, not limited to the specific detailed representative apparatus and illustrative examples shown and described. Accordingly, departures may be made from such details without departing from the spirit or scope of applicant's general inventive concept.

What is claimed is:

1. A collimator for a computed tomographic X-ray scanner including:
   (a) a plurality of generally rectangular blades of X-ray beam stopping material each having a longitudinal slot for passing X-rays from a source to a target, said plurality of blades being mounted in star-shaped configuration lengthwise along a rotatable axle;
   (b) motor means for rotating said star-shaped configuration of blades; and
   (c) means for minimizing vibration of said blades while maximizing the proximity of said slots to one lengthwise edge of each of said blades, said means comprising an X-ray penetrable reinforcing member affixed to each said blade to extend transversely across at least a portion of each of said slots.

2. A collimator for a computed tomographic X-ray scanner including:
   (a) a plurality of blades of X-ray beam stopping material each having a longitudinal slot for passing X-rays from a source to a target, said plurality of blades being mounted in star-shaped configuration lengthwise along a rotatable axle;
   (b) motor means for rotating said star-shaped configuration of blades; and
   (c) an X-ray penetrable reinforcing member affixed to each said blade to extend transversely across a portion of its slot and thereby rigidify each of said blades.

3. A collimator for a computed tomographic X-ray scanner comprising a plurality of blades of X-ray beam stopping material, each blade having an aperture for passing X-rays and an X-ray penetrable member closing at least a portion of said aperture to reinforce said blade, said plurality of blades being mounted in star-shaped configuration lengthwise along a rotatable axle, and motor means for rotating said star-shaped configuration of blades.

4. A collimator of claim 3 wherein said aperture is fixed in size and shape.

5. A collimator of claim 1, 2 or 3 wherein said X-ray penetrable members are each affixed to an exterior surface of a corresponding blade.

6. A collimator of claim 1, 2 or 3 including two of said X-ray penetrable members for each blade, one affixed to one exterior surface of each corresponding blade and the other affixed to an opposing exterior surface.

7. A collimator of claim 6 wherein said exterior surfaces are substantially flat and said X-ray penetrable members each comprise a flat plate of X-ray penetrable material.

8. A collimator of claim 1, 2 or 3 wherein said X-ray penetrable members each comprises X-ray penetrable material selected from the group consisting of: plastic, beryllium, graphite reinforced epoxy, and aluminum.

9. A collimator of claim 1, 2 or 3 wherein said X-ray penetrable member absorbs X-rays in a selected energy region of the X-ray spectrum.

10. A collimator of claim 9 wherein said member comprises X-ray penetrable material selected from the group consisting of copper, stainless steel, and titanium.

11. A collimator of claim 2 wherein each said blade has two lengthwise edges and said slot of each blade is located closer to one of said lengthwise edges of said blades than the other.

12. A collimator of claim 3 wherein each said blade has two lengthwise edges and said aperture is located closer to one of said lengthwise edges of said blade than the other.

* * * * *